United States Patent
Taylor

(10) Patent No.: US 6,187,317 B1
(45) Date of Patent: Feb. 13, 2001

(54) NATURAL ANTI-DIARRHEAL COMPOSITION AND METHOD

(76) Inventor: Judith Taylor, 2 Fairview Pl., Brooklyn, NY (US) 11226

(*) Notice: Under 35 U.S.C. 154(b), the term of this patent shall be extended for 0 days.

(21) Appl. No.: 09/353,327

(22) Filed: Jul. 14, 1999

(51) Int. Cl.⁷ .................... A61K 35/78; A61K 33/10
(52) U.S. Cl. ................ 424/195.1; 424/717; 514/867
(58) Field of Search .................... 424/195.1, 717; 514/867

(56) References Cited

U.S. PATENT DOCUMENTS

| | | | |
|---|---|---|---|
| 3,928,574 | * 12/1975 | Phillips | 424/629 |
| 4,465,667 | 8/1984 | Byröd et al. | 424/686 |
| 4,689,319 | * 8/1987 | Phillips et al. | 514/25 |
| 4,942,042 | * 7/1990 | Bhargava et al. | 424/683 |
| 5,038,396 | * 8/1991 | Gjerlov | 424/195.1 |
| 5,124,144 | 6/1992 | Giorgetti et al. | 424/78.01 |
| 5,171,575 | * 12/1992 | Shibata et al. | 424/442 |
| 5,232,698 | 8/1993 | Hord | 424/195.1 |
| 5,234,916 | 8/1993 | Hord | 514/57 |

FOREIGN PATENT DOCUMENTS

3930849 * 3/1991 (DE).

* cited by examiner

Primary Examiner—Christopher Tate
(74) Attorney, Agent, or Firm—Steven Horowitz

(57) ABSTRACT

A safe and very effective orally administered homeopathic anti-diarrheal composition and method that can be used by persons of any age, including an infant, a child, an adult or the elderly. Useful for even severe diarrhea. Normal bowel movement is resumed within two to three days. The composition consists of sodium bicarbonate and lemon juice proportionately combined. In a preferred embodiment between one quarter and one third of a teaspoon of sodium bicarbonate, commonly called baking soda, is added to the amount of lemon juice that results from thoroughly squeezing by hand one half of an average sized fresh lemon. A lime can be substituted for a lemon in the composition with the same or similar results. The composition should be taken orally at least once every 12 hours up to two times per day.

9 Claims, No Drawings

NATURAL ANTI-DIARRHEAL COMPOSITION AND METHOD

The present invention is a safe and effective composition and method for treating diarrhea.

Diarrhea is a well known problem in humans that can disrupt normal bowel movement of adults, children, infants and the elderly. Various remedies have been put forth, some natural or homeopathic such as bananas and others that are based on over the counter medications such as Kaopectate or even prescription drugs.

Unfortunately, to date, no remedy is safe and effective and satisfies all the criteria desirable in an anti-diarrheal remedy. For example, the prescription drug remedies always have side effects. On the other hand, the homeopathic remedies are not fully reliably effective and as explained further below, they are not as effective as the present invention.

With respect to prospective remedies that can alleviate diarrhea in humans, it is desirable that the remedy be made of natural ingredients, that it be powerfully effective within a reasonable amount of time, that it be effective for all levels of severity of the diarrhea, that it be easy to prepare, that it be made from easily accessibly ingredients, that it be usable on people of all ages including the elderly, children, infants and adults, and that it be safe and effective for both healthy and ill individuals. The present invention meets all of these criteria.

Lemon is believed to have some effectiveness as an anti-flatulence food. Sodium bicarbonate is known for a number of things including as a laxative. Both are well known to be safe within reasonable limits on quantity. The present invention is a composition for fighting diarrhea based on lemon (or lime) and sodium bicarbonate.

The following important objectives and advantages of the present invention are:

(A) to provide a safe and effective remedy for diarrhea and one which achieves normal bowel movement within two to three days or less, (B) to provide a natural homeopathic remedy for diarrhea, (C) to provide a remedy for diarrhea that is effective for all levels of severity of the diarrhea, (D) to provide a remedy for diarrhea that is very easy to prepare, (E) to provide a remedy for diarrhea that is based on easily accessible ingredients, (F) to provide a remedy for diarrhea that can be used for the elderly, for children and infants and for adults, and (G) to provide a remedy for diarrhea that is safe and effective for both healthy and ill individuals.

DETAILED DESCRIPTION OF THE PREFERRED EMBODIMENT

There are essentially two ingredients of the composition of the present invention. The first ingredient is baking soda, whose chemical name is sodium bicarbonate. An example of an acceptable form of sodium bicarbonate is the baking soda sold by a company called Arm & Hammer.

The second ingredient is juice squeezed out of a fresh lemon or a fresh lime. The amount of juice used as the second ingredient is, if lemon juice, equal to approximately the amount of lemon juice that is squeezed out of one half of an average-sized lemon by thoroughly squeezing the half of the lemon by hand. Similarly, the amount of juice used as the second ingredient is, if lime juice, equal to approximately the amount of lime juice that is squeezed out of one half of an average-sized lime by thoroughly squeezing the half of the lime by hand. This amount of lemon juice or lime juice is a fixed quantity in the composition of the present invention. The amount of the second ingredient will, however, vary depending on the age of the individual ingesting the composition.

The amount of sodium bicarbonate to be used varies with the age of the person using the composition. For adults, the ideal amount of sodium bicarbonate used with the fixed quantity of lemon juice or lime juice described above is between approximately one quarter of a teaspoon and approximately one third of a teaspoon. If more than one third but less than one half of a teaspoon of sodium bicarbonate were used in the composition to be given to an adult the composition would actually be too effective in the sense that it would be likely to cause constipation. Moreover, if more than one half of a teaspoon of sodium bicarbonate were used it would certainly cause constipation and would be inadvisable.

For children between approximately the ages of 8 and 12, the ideal amount of sodium bicarbonate used with the fixed quantity of lemon juice or lime juice described above is between approximately one eighth of a teaspoon and approximately one quarter of teaspoon. If more than one quarter but less than one third of a teaspoon of sodium bicarbonate were used in the composition to be given to a child between 8 and 12 years old, it would be too effective in the sense that it could cause constipation. If more than one third of a teaspoon of sodium bicarbonate were used it would cause constipation for sure and would be inadvisable. If between one sixteenth and one eighth of a teaspoon of sodium bicarbonate were used it would be less effective in the sense that it would take longer to resume normal bowel movement.

For children up to the age of 8, the ideal amount of sodium bicarbonate used with the fixed quantity of lemon juice or lime juice is approximately one eighth of a teaspoon. This amount could vary slightly depending on the age of the child. A very young infant would need less than a seven year old. If more than one eighth but less than one third of a teaspoon of sodium bicarbonate were used in the composition for children under the age of 8, it would be too effective in the sense that it could cause constipation. If a more than one third of a teaspoon of sodium bicarbonate were used it would cause constipation for sure and would be inadvisable. If between one sixteenth and one eighth of a teaspoon of sodium bicarbonate were used it would be less effective in the sense that it would take longer to resume normal bowel movement.

PREPARATION AND METHOD OF CONSUMPTION OF THE COMPOSITION

The composition of the present invention should be mixed by combining the two ingredients into a cup or other container and stirring the contents until the mixture fizzes. The composition should then be sipped gradually. The composition should be taken at least once every twelve hours but should not be taken more than twice per day. After sipping the entire contents of the composition, it has been found that drinking a little water can generate a soothing result, although such drinking is not required in order to gain the benefit of the composition of the present invention.

The composition of the present invention was tested on many people of all ages and varying nationalities and races over a period of many years, both healthy individuals and patients who are ill. The preferred proportion will yield an improved bowel movement condition in only a few hours and will result in completely normal bowel movement within two to three days even with severe cases of diarrhea. The fact that it does not work instantly is a testament to the fact that the composition operates without harmful side effects and within the body's natural healing process.

The composition of the present invention may be used at any time of day. It is recommended however that the composition be used after a light meal because the composition has a fizz and taking in gaseous material on an empty stomach might cause discomfort.

Although the present invention has been described in detail in the foregoing specification with respect to various embodiments thereof, the specification is intended to be illustrative only and not limiting. One skilled in the art will recognize that various modifications and variations may be made therein which are within the spirit of the invention and the scope of the appended claims.

What is claimed is:

1. A method of treating diarrhea in adult humans comprising:
    (i) placing between approximately one quarter of a teaspoon and approximately one third of a teaspoon of sodium bicarbonate in a cup,
    (ii) adding lemon or lime juice from a fresh lemon or lime in an amount equal to approximately the amount of juice that is squeezed out of one-half of an average-sized lemon or lime by thoroughly squeezing the half of lemon or lime by hand to the cup,
    (iii) stirring the mixture until fizzing develops, and
    (iv) sipping the mixture at least once every twelve hours but no more than two times per day.

2. The method of claim 1, wherein the juice added in step (ii) is lemon juice.

3. The method of claim 1, wherein the juice added in step (ii) is lime juice.

4. A method of treating diarrhea in children between the age of 8 and 12 comprising:
    (i) placing between approximately one eighth of a teaspoon and approximately one quarter of a teaspoon of sodium bicarbonate in a cup,
    (ii) adding lemon or lime juice from a fresh lemon or lime in an amount equal to approximately the amount of juice that is squeezed out of one-half of an average-sized lemon or lime by thoroughly squeezing the half of lemon or lime by hand to the cup,
    (iii) stirring the mixture until fizzing develops, and
    (iv) sipping the mixture at least once every twelve hours but no more than two times per day.

5. The method of claim 4, wherein the juice added in step (ii) is lemon juice.

6. The method of claim 4, wherein the juice added in step (ii) is lime juice.

7. A method of treating diarrhea in children younger than 8 years comprising:
    (i) placing approximately one eighth of a teaspoon of sodium bicarbonate in a cup,
    (ii) adding lemon or lime juice from a fresh lemon or lime in an amount equal to approximately the amount of juice that is squeezed out of one-half of an average-sized lemon or lime by thoroughly squeezing the half of lemon or lime by hand to the cup,
    (iii) stirring the mixture until fizzing develops, and
    (iv) sipping the mixture at least once every twelve hours but no more than two times per day.

8. The method of claim 7, wherein the juice added in step (ii) is lemon juice.

9. The method of claim 7, wherein the juice added in step (ii) is lime juice.

* * * * *